US011758091B2

(12) United States Patent
Lee et al.

(10) Patent No.: US 11,758,091 B2
(45) Date of Patent: Sep. 12, 2023

(54) FOOD MONITORING APPARATUS, REFRIGERATOR INCLUDING THE SAME, AND OPERATING METHOD THEREOF

(71) Applicants: SAMSUNG ELECTRONICS CO., LTD., Suwon-si (KR); CHUNG ANG University Industry Academic Cooperation Foundation, Seoul (KR)

(72) Inventors: Suyeon Lee, Seoul (KR); Jeongsu Han, Hwaseong-si (KR); Unjeong Kim, Osan-si (KR); Hyungbin Son, Seoul (KR); Junhoe Choi, Hwaseong-si (KR)

(73) Assignees: SAMSUNG ELECTRONICS CO., LTD., Suwon-si (KR); CHUNG ANG University Industry Academic Cooperation Foundation, Seoul (KR)

( * ) Notice: Subject to any disclaimer, the term of this patent is extended or adjusted under 35 U.S.C. 154(b) by 0 days.

(21) Appl. No.: 17/366,695

(22) Filed: Jul. 2, 2021

(65) Prior Publication Data
US 2022/0191432 A1 Jun. 16, 2022

(30) Foreign Application Priority Data
Dec. 11, 2020 (KR) .......................... 10-2020-0173505

(51) Int. Cl.
| | |
|---|---|
| F25D 27/00 | (2006.01) |
| F25D 29/00 | (2006.01) |
| G01N 33/02 | (2006.01) |
| G06T 7/00 | (2017.01) |
| H04N 7/18 | (2006.01) |

(52) U.S. Cl.
CPC ............ *H04N 7/18* (2013.01); *F25D 27/005* (2013.01); *F25D 29/005* (2013.01); *G01N 33/02* (2013.01);
(Continued)

(58) Field of Classification Search
CPC ....... H04N 7/18; F25D 27/005; F25D 29/005; F25D 2600/04; F25D 2700/06; G01N 33/02; G06T 7/0002; G06T 2207/10152
(Continued)

(56) References Cited

U.S. PATENT DOCUMENTS

| | | | |
|---|---|---|---|
| 5,088,822 | A | 2/1992 | Kanda |
| 5,793,879 | A | 8/1998 | Benn et al. |

(Continued)

FOREIGN PATENT DOCUMENTS

| | | |
|---|---|---|
| CN | 110987885 A | 4/2020 |
| CN | 1100956217 A | 4/2020 |

(Continued)

OTHER PUBLICATIONS

Siche Raul et al, Evalutaion of Food Quality and Safety with Hypersepctral Imaging (HSI), Nov. 2015, Food Engineering Reviews, Springer, US, vol. 8 No. 3, pp. 306-322. (Year: 2015).*

(Continued)

*Primary Examiner* — John W Miller
*Assistant Examiner* — Omer Khalid
(74) *Attorney, Agent, or Firm* — Sughrue Mion, PLLC (57) ABSTRACT

Provided is a food monitoring apparatus including at least one light source configured to selectively radiate light of a first wavelength band and light of a second wavelength band that is different from the first wavelength band to food, at least one image sensor configured to obtain a visible image of the food and a hyperspectral image of the food based on light scattered, emitted, or reflected from the food, and at least one processor configured to obtain first information of the food based on the visible image, and to obtain second information of the food based on the first information and the hyperspectral image.

20 Claims, 6 Drawing Sheets

(52) U.S. Cl.
CPC ........ *G06T 7/0002* (2013.01); *F25D 2600/04* (2013.01); *F25D 2700/06* (2013.01); *G06T 2207/10152* (2013.01)

(58) Field of Classification Search
USPC ......................................................... 348/131
See application file for complete search history.

(56) References Cited

U.S. PATENT DOCUMENTS

| | | | |
|---|---|---|---|
| 10,628,660 B2* | 4/2020 | Adato | G06Q 30/0639 |
| 2014/0267684 A1 | 9/2014 | Nelson et al. | |
| 2014/0293277 A1 | 10/2014 | Subbiah et al. | |
| 2014/0300891 A1 | 10/2014 | Alfano et al. | |
| 2020/0088463 A1* | 3/2020 | Jeong | G06F 3/011 |
| 2020/0088579 A1* | 3/2020 | Balas | G01J 3/2823 |
| 2020/0097776 A1* | 3/2020 | Kim | H04N 23/60 |
| 2022/0091087 A1 | 3/2022 | Kim et al. | |

FOREIGN PATENT DOCUMENTS

| | | |
|---|---|---|
| JP | 2002-162358 A | 6/2002 |
| JP | 2014-153163 A | 8/2014 |
| JP | 2020-076644 A | 5/2020 |

OTHER PUBLICATIONS

Communication dated Apr. 20, 2022, issued by the European Patent Office in counterpart European Application No. 21203948.1.
Raul Siche et al., "Evaluation of Food Quality and Safety with Hyperspectral Imaging (HSI)," Springer, Food Engineering Reviews (2016), vol. 8, No. 3, pp. 306-322, Nov. 2015, XP036028885.
Dheni Mita Mala et al., "Fiber optics fluorescence fingerprint measurement for aerobic plate count prediction on sliced beef surface", LWT—Food Science and Technology, 2016, vol. 68, pp. 14-20 (7 pages total) avail online Dec. 8, 2015.
Seoho Lee et al., "NIR spectroscopic sensing for point-of-need freshness assessment of meat, fish, vegetables and fruits", SPIE, May 1, 2017, vol. 1021708, pp. 1021708-1-1021708-7 (8 pages total).
Yang Pu et al., "Spoilage of foods monitored by native fluorescence spectroscopy with selective excitation wavelength", SPIE, Mar. 12, 2015, vol. 9314, pp. 93140V-1-93140V-11 (12 pages total).
Jaegone Kim et al., "Fluorescence Based Spectral Assessment of Pork Meat Freshness", Food Engineering Progress, Aug. 25, 2012, vol. 16, No. 3, pp. 249-256 (8 pages total).
A. Aït-Kaddour et al., "Potential of fluorescence spectroscopy to predict fatty acid compostion of beef", Meat Science, 2016, vol. 113, pp. 124-131 (8 pages total) (online Nov. 24, 2015).

\* cited by examiner

FOOD MONITORING APPARATUS, REFRIGERATOR INCLUDING THE SAME, AND OPERATING METHOD THEREOF

CROSS-REFERENCE TO RELATED APPLICATION

This application is based on and claims priority under 35 U.S.C. § 119 to Korean Patent Application No. 10-2020-0173505, filed on Dec. 11, 2020, in the Korean Intellectual Property Office, the disclosure of which is incorporated by reference herein in its entirety.

BACKGROUND

1. Field

Example embodiments of the present disclosure relate to food monitoring apparatuses, refrigerators including the same, and operating method of the same.

2. Description of Related Art

Technology of acquiring information about food and analyzing characteristics or conditions of food based on the acquired information is widely used not only for research purposes but also for the purpose of providing convenience to users.

Among conventional methods of analyzing the state of food, a method of preparing a sample by pulverizing food, and measuring a pH of the sample, a volatile basic nitrogen (VBN) content, and the number of microorganisms may be suitable for measuring the freshness of food, but may not be suitable for general consumers because the food to be measured is destroyed. Therefore, there is a need for a technology that accurately provides information on the condition of food without destroying the food to be measured.

SUMMARY

One or more example embodiments provide food monitoring apparatuses, refrigerators including the same, and operating methods of the food monitoring apparatuses.

The technical problem to be achieved by the present disclosure is not limited to the technical problems as described above, and other technical problems may be inferred from the following example embodiments.

Additional aspects will be set forth in part in the description which follows and, in part, will be apparent from the description, or may be learned by practice of example embodiments.

According to an aspect of an example embodiment, there is provided a food monitoring apparatus including at least one light source configured to selectively radiate light of a first wavelength band and light of a second wavelength band that is different from the first wavelength band to food, at least one image sensor configured to obtain a visible image of the food and a hyperspectral image of the food based on light scattered, emitted, or reflected from the food, and at least one processor configured to obtain first information of the food based on the visible image, and to obtain second information of the food based on the first information and the hyperspectral image.

The at least one processor may be further configured to correct at least one of the hyperspectral image, parameters used to analyze the hyperspectral image, and a correlation between the parameters and the second information based on the first information.

The first information may include at least one of a type of the food and a part of the food, and the at least one processor may be further configured to selectively apply a weight to the parameters based on the first information, and obtain the second information by analyzing the hyperspectral image based on the parameters to which the weight is applied.

The first information may include a packaging condition of the food, and the at least one processor may be further configured to correct the parameters based on the packaging condition, and obtain the second information based on the corrected parameters.

The parameters may include at least one of 1,4-dihydronicotinamide adenine dinucleotide (NADH) content, porphyrin content, flavin adenine dinucleotide (FAD) content, and collagen content included in the food.

The first information may include a location of the food in the food monitoring apparatus, and the at least one processor may be further configured to control the at least one light source to radiate the light of the second wavelength band to an area of the food monitoring apparatus corresponding to the location of the food, and obtain the hyperspectral image from light received from the area of the food monitoring apparatus corresponding to the location of the food.

The first wavelength band may range from 400 nm to 700 nm, the second wavelength band may range from 250 nm to 400 nm, and the at least one image sensor may be further configured to measure light in a wavelength band ranging from 300 nm to 700 nm.

According to another aspect of an example embodiment, there is provided a refrigerator including a main body including a storage space, a door configured to open and close the storage space, and the food monitoring apparatus that is disposed in the storage space.

The second information may include at least one of freshness, maturity, and spoilage of the food, and the at least one processor may be further configured to determine at least one of whether the food is edible, an intakeable period of the food, an optimum intake time of the food, and a cooking method of the food based on the at least one of the freshness, maturity, and spoilage of the food.

The refrigerator may further include a controller including at least one processor and configured to control at least one of temperature, humidity, and gas composition ratio in the storage space.

The second information may include maturity of the food, and the at least one processor is further configured to determine whether acceleration or deceleration of maturation of the food may be necessary to reach a target maturation at a preset intake time of the food based on the maturity of the food, and control the at least one of temperature, humidity, and gas composition ratio in the storage space by the controller.

When it is determined that acceleration or deceleration of maturation of the food is necessary, the at least one processor may be further configured to increase or decrease a temperature in the storage space from a preset temperature during at least a portion of a period between a time when the maturity of the food is determined and the preset intake time.

The refrigerator may further include a display device disposed on the door of the food monitoring apparatus, the display device configured to output the second information received from the food monitoring apparatus.

The refrigerator may further include a communication interface configured to communicate with an external device to transmit the second information to the external device.

According to yet another aspect of an example embodiment, there is provided a method of operating a food monitoring apparatus, the method including selectively radiating light of a first wavelength band and light of a second wavelength band that is different from the first wavelength band to food by at least one light source, obtaining a visible image of the food and a hyperspectral image of the food based on light scattered, emitted, or reflected from the food by at least one image sensor, obtaining first information of the food based on the visible image, and obtaining second information of the food based on the first information and the hyperspectral image.

The obtaining of the second information may include correcting at least one of the hyperspectral image, parameters used to analyze the hyperspectral image, and a correlation between the parameters and the second information based on the first information.

The first information may include at least one of a type of the food and a part of the food, and the obtaining of the second information may include selectively applying a weight to the parameters based on the first information, and obtaining the second information by analyzing the hyperspectral image based on the parameters to which the weight is applied.

The first information may include a packaging condition of food, and the obtaining of the second information may include correcting the parameters based on the packaging condition, and obtaining the second information based on the corrected parameters.

The parameters may include at least one of 1,4-dihydronicotinamide adenine dinucleotide (NADH) content, porphyrin content, flavin adenine dinucleotide (FAD) content, and collagen content in the food.

The first information may include a location of the food in the food monitoring apparatus, and the obtaining of the visible image of the food or the hyperspectral image of the food may include controlling the at least one light source to radiate light of the second wavelength band to an area of the food monitoring apparatus corresponding to the location of the food, and obtaining the hyperspectral image based on light received from the area of the food monitoring apparatus corresponding to the location of the food.

According to an aspect of an example embodiment, there is provided a food monitoring apparatus including at least one light source configured to selectively radiate light of a first wavelength band and light of a second wavelength band that is different from the first wavelength band to food, at least one image sensor configured to obtain a visible image of the food and a hyperspectral image of the food based on light scattered, emitted, or reflected from the food, and at least one processor configured to obtain first information of the food based on the visible image, obtain second information of the food based on the first information and the hyperspectral image, and correcting the hyperspectral image based on the first information.

BRIEF DESCRIPTION OF THE DRAWINGS

The above and/or other aspects, features, and advantages of example embodiments will be more apparent from the following description taken in conjunction with the accompanying drawings, in which.

DETAILED DESCRIPTION

Reference will now be made in detail to example embodiments of which are illustrated in the accompanying drawings, wherein like reference numerals refer to like elements throughout. In this regard, example embodiments may have different forms and should not be construed as being limited to the descriptions set forth herein. Accordingly, the example embodiments are merely described below, by referring to the figures, to explain aspects. As used herein, the term "and/or" includes any and all combinations of one or more of the associated listed items. Expressions such as "at least one of," when preceding a list of elements, modify the entire list of elements and do not modify the individual elements of the list. For example, the expression, "at least one of a, b, and c," should be understood as including only a, only b, only c, both a and b, both a and c, both b and c, or all of a, b, and c.

Terminologies used herein are selected as commonly used by those of ordinary skill in the art in consideration of functions of example embodiments, but may vary according to the technical intention, precedents, or a disclosure of a new technology. Also, in particular cases, some terms are arbitrarily selected by the applicant, and in this case, the meanings of the terms will be described in detail at corresponding parts of the specification. Accordingly, the terms used in the specification should not be simply interpreted based on their names but based on the meaning and content of the whole specification.

As used herein, the singular forms "a," "an" and "the" are intended to include the plural forms as well, unless the context clearly indicates otherwise. It should be understood that, when a part "comprises" or "includes" an element in the specification, unless otherwise defined, other elements are not excluded from the part and the part may further include other elements.

It will be further understood that the term "comprises" or "includes" should not be construed as necessarily including various constituent elements and various operations described in the specification, and also should not be construed that portions of the constituent elements or operations of the various constituent elements and various operations may not be included or additional constituent elements and operations may further be included.

It will be understood that, although the terms "first", "second", etc. may be used herein to describe various constituent elements, these constituent elements should not be limited by these terms. These terms are only used to distinguish one constituent element from another.

The descriptions of the example embodiments should not be interpreted as limiting the scope of right, and embodiments that are readily inferred from the detailed descriptions and embodiments by those of ordinary skill in the art will be construed as being included in the inventive concept. Reference will now be made in detail to example embodiments which are illustrated in the accompanying drawings.

Figure 1:
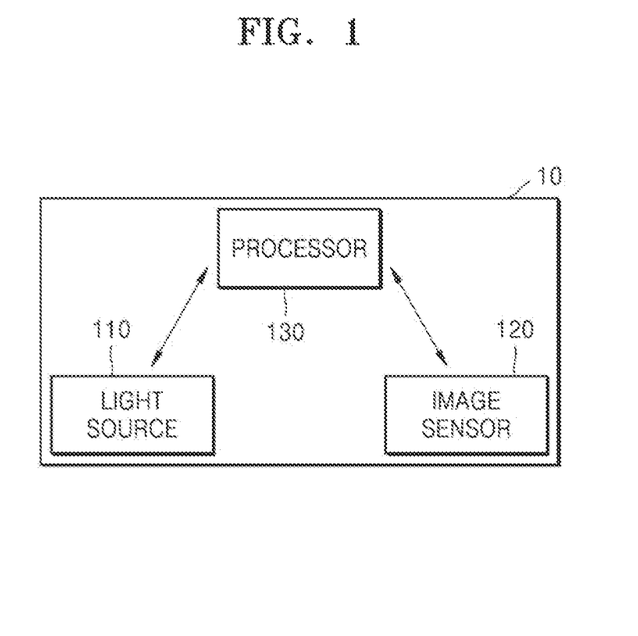
FIG. 1 is a block diagram illustrating an example of a food monitoring apparatus according to example embodiments.

FIG. 1 is a block diagram illustrating an example of a food monitoring apparatus 10 according to example embodiments.

The food monitoring apparatus 10 may be applicable to any apparatus that determines the state of food without limitation. For example, the food monitoring apparatus 10 may correspond to an apparatus that determines the state of food by being disposed in a food storage apparatus, such as a refrigerator, a kimchi refrigerator, a warmer, a storage container, a sealed container, etc., but embodiments are not limited thereto. The food monitoring apparatus 10 may correspond to an apparatus used to analyze the state of food for research purposes. Food refers to food that a person consumes on a daily basis, and may include, for example, meat, fish, eggs, grains, vegetables, fruits, dairy products, etc.

Referring to FIG. 1, the food monitoring apparatus 10 may include at least one light source 110, at least one image sensor 120, and at least one processor 130. However, only components related to the example embodiments are shown in the food monitoring apparatus 10 shown in FIG. 1. Therefore, the food monitoring apparatus 10 may further include other general-purpose components in addition to the components shown in FIG. 1. For example, the food monitoring apparatus 10 may further include a memory.

Moreover, when the object of the present disclosure is achieved even if only some of the components shown in FIG. 1 are included, an apparatus including only some of the components shown in FIG. 1 also corresponds to the food monitoring apparatus 10. For example, the food monitoring apparatus 10 may include only the at least one image sensor 120 and the at least one processor 130, and the at least one light source 110 may be disposed outside the food monitoring apparatus 10.

The memory may be hardware that stores various types of data processed by the food monitoring apparatus 10, for example, the memory may store data processed by the food monitoring apparatus 10 and data to be processed. In addition, the memory may store applications, drivers, etc. to be driven by the food monitoring apparatus 10.

Memory may include random access memory (RAM), such as dynamic random access memory (DRAM), static random access memory (SRAM), read-only memory (ROM), electrically erasable programmable read-only memory (EEPROM), CD-ROM, Blu-ray or other optical disk storage, hard disk drive (HDD), solid state drive (SSD), or flash memory, and also other external storage devices that may be accessed in the food monitoring apparatus 10.

The at least one light source 110 may refer to a device for radiating light on food. The at least one light source 110 may radiate light of a plurality of different wavelength bands to the food. For example, the at least one light source 110 may selectively radiate light of a first wavelength band and light of a second wavelength band that is different from the first wavelength band to the food. The first wavelength band may range, for example, from about 400 nm to about 700 nm, and the second wavelength band may range, for example, from about 250 nm to about 400 nm.

For example, the at least one light source 110 may be a light-emitting diode (LED) or a fluorescent lamp that radiates broad light in a visible light band, or may be a laser diode that radiates strong light with a short wavelength. However, embodiments are not necessarily limited thereto. The at least one light source 110 may emit light of a wavelength band suitable for acquiring first information or second information about food.

Also, the at least one light source 110 may be a single light source configured to selectively radiate light of a plurality of different wavelength bands on the food. However, embodiments are not limited thereto, and the at least one light source 110 may include a plurality of light sources, each of which may radiate light of one wavelength band. Also, the at least one light source 110 may include a plurality of light sources capable of selectively radiating light of a plurality of different wavelength bands to food.

The at least one image sensor 120 may refer to a device for acquiring a visible image or a hyperspectral image of the food from light scattered, emitted or reflected from the food. In one example, the at least one image sensor 120 may obtain a visible image or a hyperspectral image of the food by measuring light in a wavelength band ranging from about 300 nm to about 700 nm. However, embodiments are not necessarily limited thereto, and the at least one image sensor 120 may measure light in an arbitrary wavelength band suitable for acquiring information about food.

For example, the at least one image sensor 120 may include a charge-coupled device (CCD) sensor, a complementary metal oxide semiconductor (CMOS) sensor, or a photodiode array capable of obtaining a visible image, but is not limited thereto. The at least one image sensor 120 may acquire a visible image including information on an appearance, such as a color or shape of food. For example, the at least one image sensor 120 may acquire an RGB image of food.

In addition, the at least one image sensor 120 may acquire a hyperspectral image including information on fluorescence emitted from food. Indicator materials in food may emit fluorescence as light is radiated from the at least one light source 110. For example, the indicator material may include at least one of 1,4-dihydronicotinamide adenine dinucleotide (NADH), porphyrin, flavin adenine dinucleotide (FAD), and collagen. NADH may denote a reduced form of nicotinamide adenine dinucleotide (NAD). Parameters representing the content of indicator materials may be obtained from the hyperspectral image, and are used to acquire second information. For example, NADH is a material produced as a result product of cellular respiration, and because it is produced only by microorganisms after an animal dies, information, such as freshness, maturity, and spoilage of food, may be obtained from the NADH content.

In addition, the at least one image sensor 120 may be a single image sensor configured to acquire a visible image or a hyperspectral image of food from light scattered, emitted, or reflected from the food. However, embodiments are not limited thereto, and the at least one image sensor 120 may include a plurality of image sensors each obtaining one visible image or a hyperspectral image of the food from light scattered, emitted, or reflected from the food. In addition, the at least one image sensor 120 may include a plurality of image sensors for acquiring a plurality of visible or hyperspectral images of the food from light scattered, emitted, or reflected from the food.

The at least one processor 130 may perform an overall function for controlling the food monitoring apparatus 10. For example, the at least one processor 130 may control the operation of the at least one light source 110 and the at least one image sensor 120. The at least one processor 130 may be implemented as an array of a plurality of logic gates, and may be implemented as a combination of a general-purpose microprocessor with a memory in which a program executable by the microprocessor is stored.

The at least one processor 130 may acquire first information on the food based on a visible image acquired from the at least one image sensor 120, and may acquire second information on the food based on the acquired first information and the hyperspectral image obtained from the at least one image sensor 120. In this way, the at least one processor 130 does not acquire the second information by using only the information acquired through the analysis of the hyperspectral image, but acquires the second information by comprehensively considering the information acquired through the analysis of the visible image, and accordingly, the accuracy of the second information on the food may be increased.

For example, the first information includes at least one of a type, a part, and a packaging condition of the food, and a position of the food in the food monitoring apparatus 10, and the second information includes at least one of freshness, maturity, and spoilage of the food. However, embodiments are not necessarily limited thereto.

The at least one processor 130 may use a recognition algorithm to identify the presence of food and acquire information on the type, part, and packaging condition of the food, and location of the food in the food monitoring apparatus 10. The recognition algorithm may correspond to a classification algorithm, a clustering algorithm, an ensemble learning algorithm, a general algorithm for predicting an arbitrary structured label, a regression algorithm, and the like.

The classification algorithm may include SVC, Naive Bayes Classifier, K-nearest Neighbors Classifier, Ensemble Classifier, SGD Classifier, kernel approximation, Neural Network, SVM, decision Trees, Logistic Regression, etc., and the clustering algorithm may include Spectral Clustering, Kmeans Clustering, MiniBatch Kmeans Clustering, and the like. Also, the ensemble learning algorithm may include Boosting (meta-algorithm), Bootstrap aggregating ("bagging"), and Ensemble averaging, the general algorithm for predicting an arbitrary structured label may include Bayesian networks and Markov random fields, and the regression algorithm may include Gaussian process regression (kriging), Linear/Nonlinear regression and extensions, Neural networks and Deep learning methods, Independent component analysis (ICA), Principal components analysis (PCA), and the like.

The neural network may include n-layers neural networks or a deep neural network (DNN) including one or more hidden layers. DNN may include Convolutional Neural Networks (CNN), Recurrent Neural Networks (RNN), Deep Belief Networks, Restricted Boltzmann Machines, and the like, but is not limited thereto. When the pattern recognition algorithm is a neural network, an estimation result of the pattern recognition algorithm may correspond to an inference result of the neural network.

The at least one processor 130 may determine freshness, maturity, and spoilage of the food based on at least one of NADH content, porphyrin content, FAD content, and collagen content in the food or the content ratio thereof. When radiating light of a specific wavelength band on the food, the at least one processor 130 may measure the NADH content based on a spectral distribution with respect to a wavelength band of, for example, about 430 nm to about 550 nm, and may measure the porphyrin content based on a spectral distribution with respect to a wavelength band of, for example, about 570 nm to about 630 nm. In addition, the at least one processor 130 may measure the FAD content based on the spectral distribution with respect to the wavelength band of, for example, about 500 nm to about 550 nm, and measure the collagen content based on the spectral distribution with respect to the wavelength band of, for example, about 360 nm to about 420 nm.

According to an example, the at least one processor 130 may correct at least one of a hyperspectral image, parameters used to analyze the hyperspectral image, and a correlation between the parameters and information about the state of food by using information acquired through the analysis of a visible image. As described later, when the information acquired through the analysis of the visible image includes a location of the food in the food monitoring apparatus, the at least one processor 130 may obtain a clearer hyperspectral image with respect to an object to be measured by allowing the at least one light source 110 to radiate light of the second wavelength band to a region corresponding to the location of the food. When the information acquired through the analysis of the visible image includes the packaging condition of the food, the at least one processor 130 may amplify the content of the parameters according to a predetermined ratio for each packaging condition. In addition, when the information acquired through the analysis of the visible image includes at least one of a type and a part of the food, the at least one processor 130 may assign a weight to the parameters. However, embodiments are not necessarily limited thereto.

In this way, the at least one processor 130 determines the state of the food not by using only the information acquired through the analysis of the hyperspectral image, but by comprehensively considering the information acquired through the analysis of the visible image. Thus, the accuracy of the condition of the food may be increased. Hereinafter, a process of operating the food monitoring apparatus 10 will be described in more detail with reference to FIG. 2.

Figure 2:
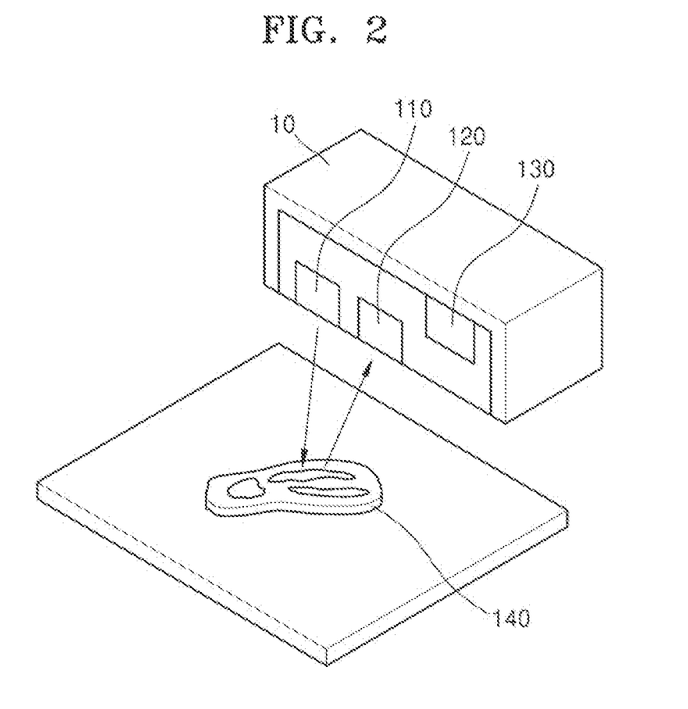
FIG. 2 is a conceptual diagram of a food monitoring apparatus according to example embodiments.

FIG. 2 is a conceptual diagram of the food monitoring apparatus 10 according to example embodiments.

Referring to FIG. 2, the conceptual diagram for explaining a process in which the food monitoring apparatus 10 of FIG. 1 determines the state of food 140 is shown. The at least one light source 110 may selectively radiate light of a first wavelength band and light of a second wavelength band that is different from the first wavelength band to the food 140, and the light may be scattered, emitted, or reflected from the food 140.

According to example embodiments, the at least one processor 130 may acquire information about the location of the food 140 based on a visible image obtained from the at least one image sensor 120, and may accurately radiate light of a second wavelength band to the location of the food 140. In this example, compared to when the light is radiated over an entire measurement space of the food monitoring apparatus 10, the light may be concentrated and radiated onto the food 140 as an object to be measured. Accordingly, signals by foods or articles other than the food 140 may be removed, and the maximum output of at least one light source 110 may be used to determine the state of the food 140, and thus, the accuracy of information about the condition of the food obtained from the spectroscopic image may be increased.

For example, when information acquired through the analysis of a visible image includes a location of the food in the food monitoring apparatus 10, the at least one processor 130 may control the at least one light source 110 to radiate light of the second wavelength band to an area corresponding to the location of the food and may acquire a hyperspectral image from light received from an area corresponding to the location of the food.

Figure 3:
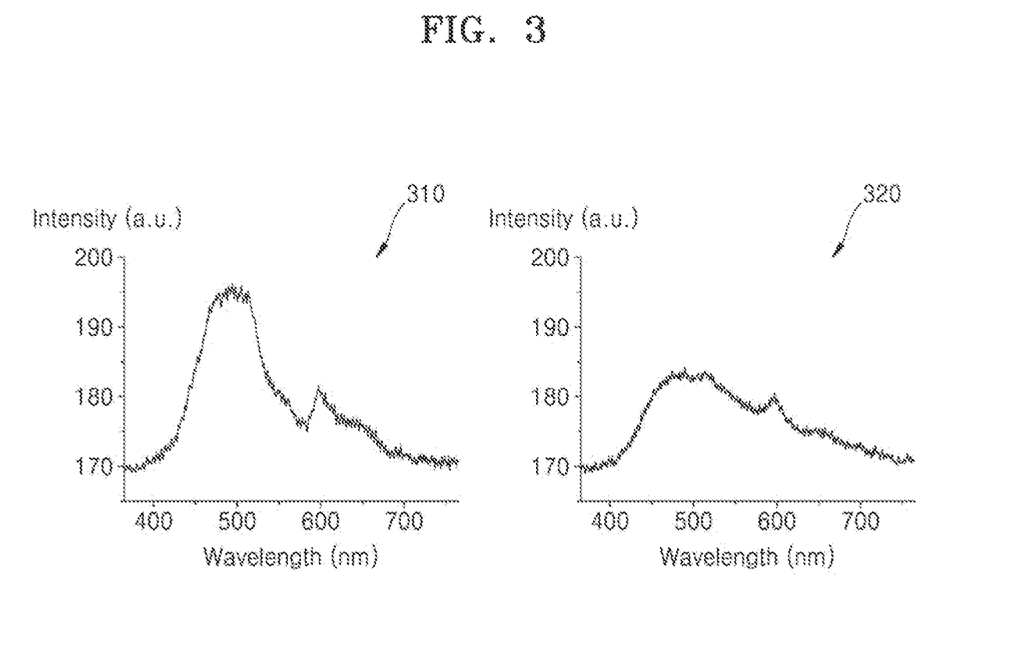
FIGS. 3 and 4 are diagrams illustrating examples of parameters obtained from hyperspectral images by different parts of food, according to example embodiments.
Figure 4:
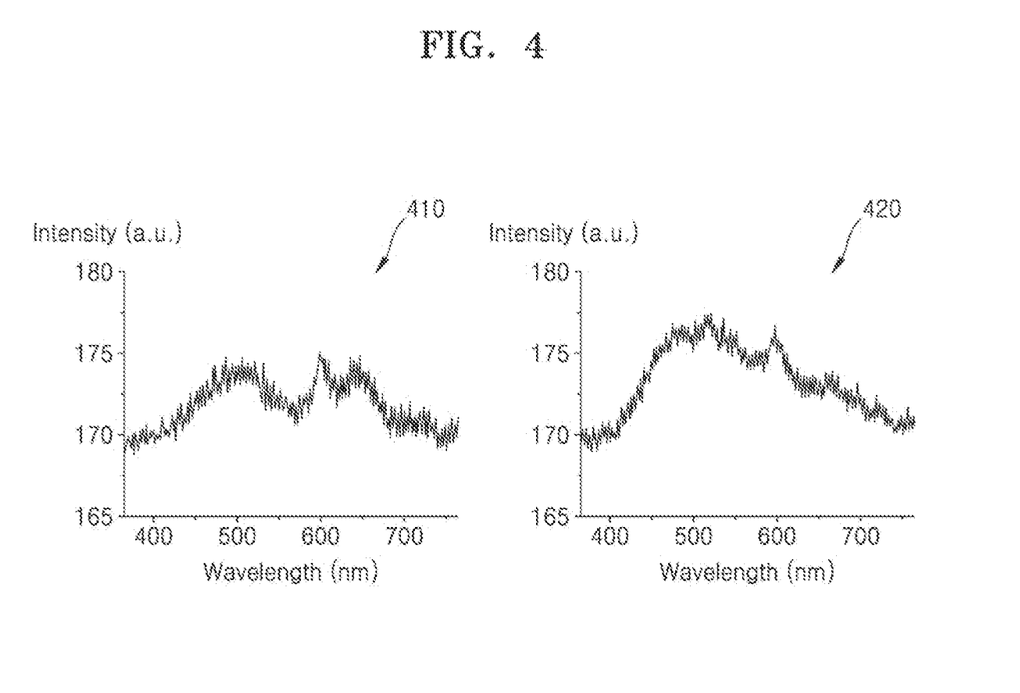

FIGS. 3 and 4 are diagrams illustrating examples of parameters obtained from hyperspectral images by different parts of food, according to example embodiments.

In FIG. 3, graphs 310 and 320 show measurement results of the intensity of light scattered, emitted, or reflected from fat tissue of meat in a wavelength band ranging from about 350 nm to about 750 nm. The graph 310 corresponds to the measurement result of fat tissue of fresh meat, and the graph 320 corresponds to the measurement result of fat tissue of decayed meat. In FIG. 4, graphs 410 and 420 show measurement results of the intensity of light scattered, emitted, or reflected from muscle tissue of meat in a wavelength band ranging from about 350 nm to about 750 nm. The graph 410 corresponds to the measurement result of the muscle tissue of the fresh meat, and the graph 420 corresponds to the measurement result of the muscle tissue of the decayed meat.

In the graphs, the intensity in the wavelength band of about 430 nm to about 550 nm corresponds to the NADH content, and the intensity in the wavelength band of about 570 nm to about 630 nm corresponds to the porphyrin content. Information on the freshness, spoilage, and maturity of the food may be obtained based on the graph pattern and the intensity in a specific wavelength band. For example, information on freshness, spoilage, and maturity of food may be obtained using the recognition algorithm described with reference to FIG. 1.

However, comparing FIGS. 3 and 4, it may be seen that the patterns of the graphs 310 and 320 in which fat tissue is measured by freshness are different from those of the graphs 410 and 420 in which the muscle tissue is measured by freshness. Therefore, the criteria for determining the freshness of food may be different depending on the part of the food.

In addition, depending on the type of food, for example, depending on whether the food to be measured is meat, fish, eggs, grains, vegetables, fruits, or dairy products, the change of aspects of the parameters may be different. Therefore, as in the case of the part of the food, the criteria for determining the freshness of the food may be different depending on the type of food. In one example, the type of food may be classified according to the porphyrin content, and the porphyrin content may be analyzed based on the color of the appearance of the food obtained from a visible image.

For example, when the information acquired through the analysis of the visible image includes at least one of a food type and a part, at least one processor (e.g., the at least one processor 110 in FIG. 1 or 2) may selectively apply weights to parameters according to the information and may acquire information on the state of the food by analyzing the hyperspectral image by using the weighted parameters. When weights are applied to parameters according to the type or part of the food, the state of the food may be determined by using parameters more suitable for analyzing the state of the food to be measured. Therefore, the accuracy of information about the state of food may be increased.

Figure 5:
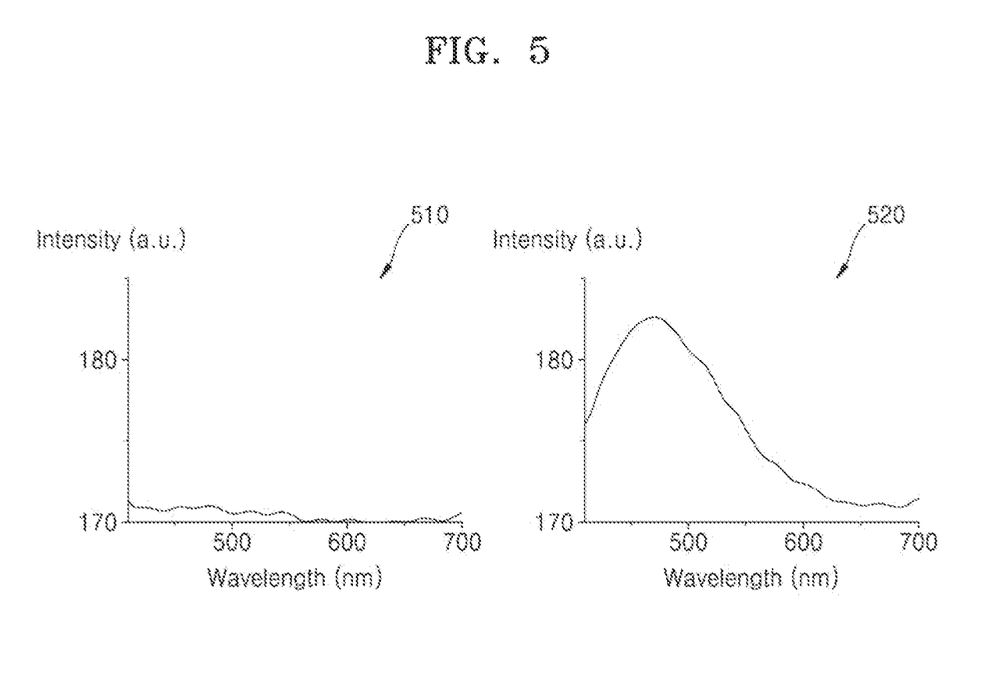
FIG. 5 is a diagram illustrating examples of data acquired from a hyperspectral image by varying a packaging state of food, according to example embodiments.

FIG. 5 is a diagram illustrating examples of data acquired from a hyperspectral image by varying the packaging state of food, according to example embodiments. Graph 510 represents data obtained with respect to vinyl wrap-packed food, and graph 520 represents data obtained for vinyl vacuum-packed food.

In the graphs 510 and 520, the intensity of light in the wavelength band of about 430 nm to about 550 nm corresponds to the NADH content, and the intensity of light in the wavelength band of about 570 nm to about 630 nm corresponds to the porphyrin content.

Referring to FIG. 5, in the example of the graph 520, compared with the graph 510, a prominent peak appears in a wavelength band of about 430 nm to about 550 nm corresponding to the NADH content. If a signal by an article other than food to be measured is not removed, the accuracy of the method of determining the state of the food may decrease, and thus, parameters must be corrected according to the packaging conditions of the food.

For example, when the information acquired through the analysis of the visible image includes the packaging condition of the food, at least one processor (e.g., the at least one processor 110 of FIG. 1 or 2) may correct the parameters based on the packing condition and acquire information about the state of the food based on the corrected parameters.

For example, when a signal by packaging is removed, a change in a pattern or parameter of a graph may become clearer, and thus, the accuracy of information about the state of the food may be increased.

In addition, when a material of a packaging material that interrupts light of the second wavelength band from being radiated to the food is present, the light of the second wavelength band may be radiated to a part of the food in which the material of the packaging material is not present. In this case, a signal emitted from a packaged part of the food to be measured may decrease. Therefore, the accuracy of information about the state of food may be increased.

Figure 6:
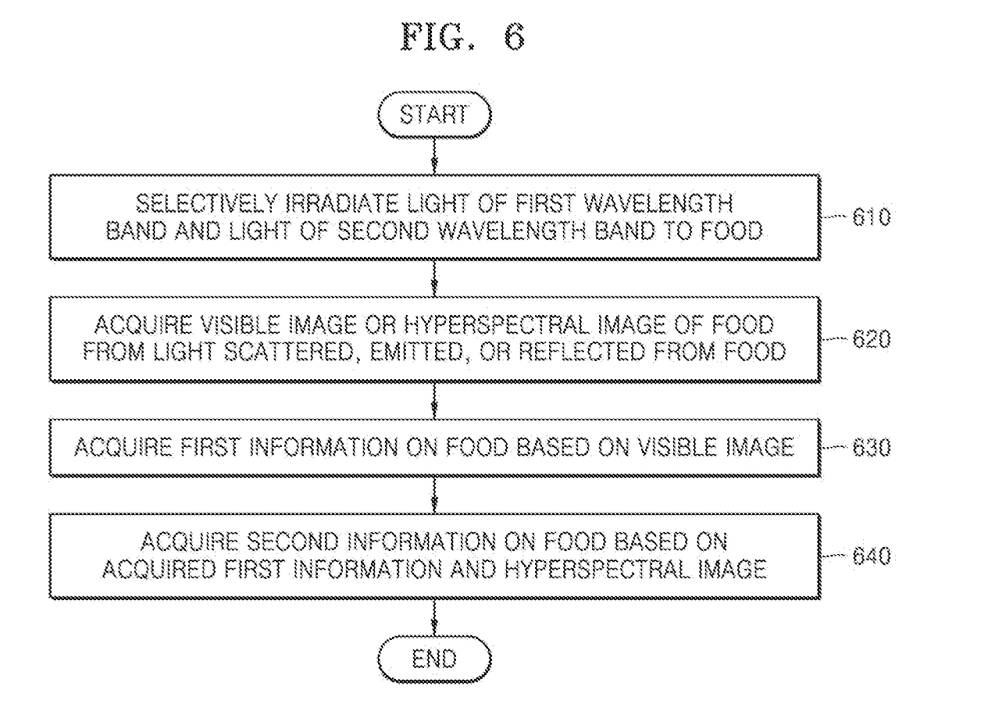
FIG. 6 is a flowchart illustrating an operating method of a food monitoring apparatus according to example embodiments.

FIG. 6 is a flowchart illustrating an operating method a food monitoring apparatus 10 according to example embodiments.

Referring to FIG. 6, a method of operating the food monitoring apparatus 10 includes operations processed in a time series in the food monitoring apparatus 10 shown in FIGS. 1 and 2. Accordingly, the descriptions given with respect to FIGS. 1 to 5, even though omitted below, may be applied to the method of operating the food monitoring apparatus of FIG. 6.

In operation 610, the food monitoring apparatus may selectively radiate light of a first wavelength band and light of a second wavelength band that is different from the first wavelength band on the food by using at least one light source.

In one example, the food monitoring apparatus may selectively radiate light in a first wavelength band in a range of about 400 nm to about 700 nm and light in a second wavelength band in a range of about 250 nm to about 400 nm by using the at least one light source. However, embodiments are not necessarily limited thereto.

In operation 620, the food monitoring apparatus may acquire a visible image or a hyperspectral image of the food from light scattered, emitted, or reflected from the food by using at least one image sensor. The at least one image sensor may acquire a visible image including information about an appearance of the food, such as color or shape. In addition, the at least one image sensor may acquire a hyperspectral image including information about fluorescence emitted from the food.

In one example, the food monitoring apparatus may measure light in a wavelength band ranging from about 300 nm to about 700 nm by using the at least one image sensor. However, embodiments are not necessarily limited thereto.

In operation 630, the food monitoring apparatus may acquire first information about the food based on the visible image. The first information may include any information necessary to accurately measure the state of the food. For example, the first information may include at least one of a type, a part, and a packaging condition of the food, and a location of the food in the food monitoring apparatus. However, embodiments are not necessarily limited thereto.

In operation 640, the food monitoring apparatus may acquire second information about the food based on the acquired first information and the hyperspectral image. The second information about the food may include all information indicating the state of the food. For example, the second information may include at least one of freshness, maturity, and spoilage of the food. However, embodiments are not necessarily limited thereto.

The food monitoring apparatus may include a correction operation correcting at least one of a hyperspectral image, parameters used to analyze the hyperspectral image, and a correlation between the parameters and the second information by using the acquired first information. For example, the parameters may include at least one of NADH content, porphyrin content, FAD content, and collagen content in food. However, embodiments are not necessarily limited thereto.

When the first information includes at least one of the type and part of the food, the food monitoring apparatus may selectively apply a weight to the parameters according to the first information, and may acquire second information by analyzing the hyperspectral image using the weighted parameters.

In addition, when the first information includes a packaging condition of the food, the food monitoring apparatus may correct parameters based on the packaging condition and acquire second information based on the corrected parameters.

When the first information includes a location of the food in the food monitoring apparatus, the food monitoring apparatus may control the at least one light source to radiate light of the second wavelength band to an area corresponding to the location of the food, and obtain a hyperspectral image from light received from the area corresponding to the location of the food.

The method of operating the food monitoring apparatus described above may be stored in a computer-readable recording medium in which one or more programs including instructions for executing the method are recorded. Examples of the computer-readable recording media include magnetic media, such as hard disks, floppy disks, and magnetic tape, optical media, such as CD-ROMs and DVDs, magneto-optical media, such as floptical disks, and hardware devices specifically configured to store and execute program instructions, such as ROM, RAM, flash memory, etc. Examples of program instructions include machine code produced by a compiler as well as high-level language code that may be executed by a computer by using an interpreter, etc.

Figure 7:
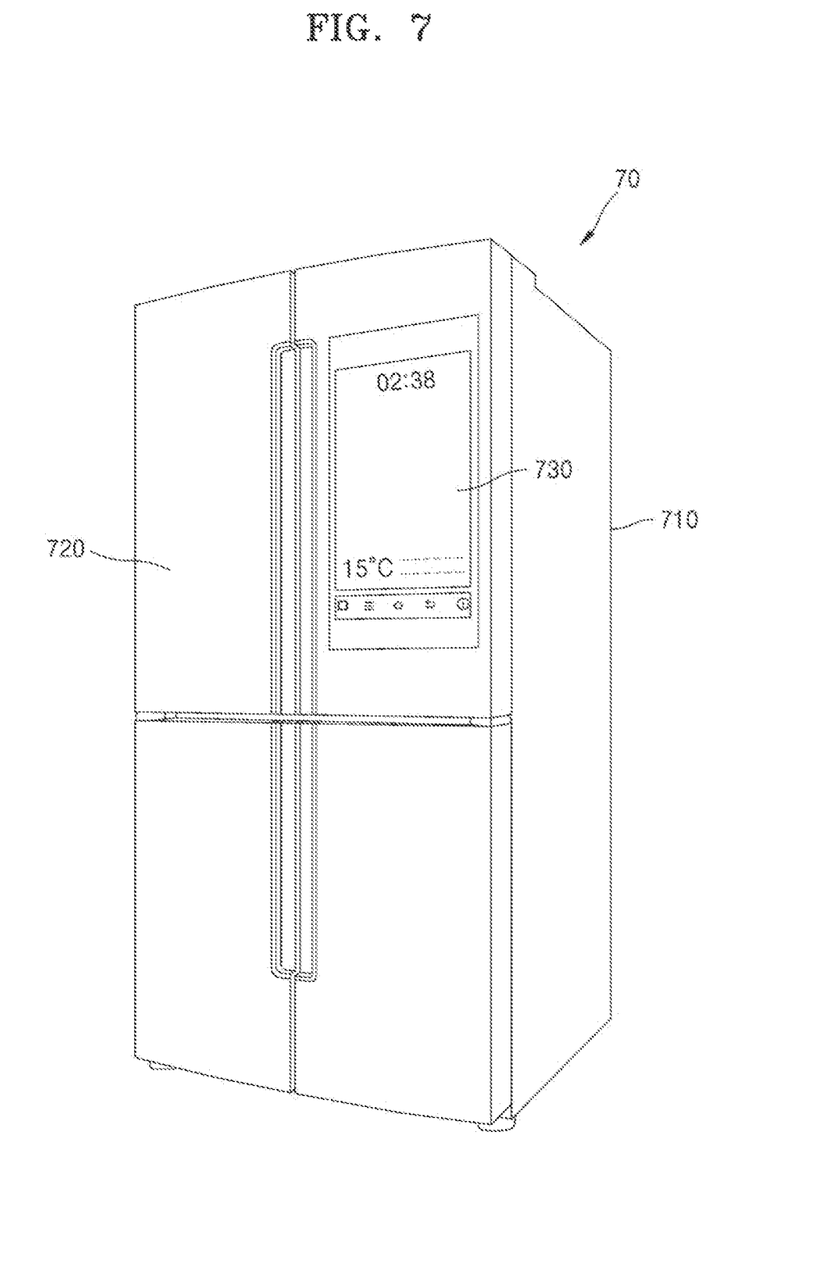
FIG. 7 is a perspective view of a refrigerator according to example embodiments.

FIG. 7 is a perspective view of a refrigerator according to example embodiments.

Referring to FIG. 7, a refrigerator 70 including a main body 710, a door 720, a display device 730, and a food monitoring apparatus may be provided. Because the food monitoring apparatus corresponds to the food monitoring apparatus 10 of FIGS. 1 and 2, repeated descriptions thereof are omitted.

The main body 710 includes a storage space, and not only one food product but also a plurality of food products may be located in the storage space. The door 720 may open and close the storage space, and thus, an environment independent from the external environment may be formed in the storage space. The display device 730 is arranged in front of the door 720 and may output second information received from the food monitoring apparatus. The display device 730 provides the second information received from the food monitoring apparatus to the user by outputting an image or audio.

According to example embodiments, when the second information includes at least one of freshness, maturity and spoilage of food, at least one processor (e.g., the at least one processor 110 of FIG. 1 or 2) included in the food monitoring apparatus may determine at least one of whether food is edible, an intake period, an optimum intake time, and a cooking method based on at least one of freshness, maturity, and spoilage. In addition, the at least one processor may provide the user with the determined possibility of whether food is edible, intake period, optimum intake time, or cooking method to the user through the display device 730.

According to example embodiments, the refrigerator 70 may further include a controller that includes at least one processor and is configured to control at least one of temperature, humidity, and gas composition ratio in the storage space. In addition, the controller controls the temperature in the storage space to be in a range of about −25° C. to about 10° C., but is not limited thereto. Because the storage space forms an environment independent from the outside, the gas composition ratio in the storage space may be controlled, and the ratio of oxygen in the gas in the storage space may be controlled.

For example, when the second information includes the maturity of the food, the at least one processor may determine whether acceleration or deceleration of maturation of the food is necessary in order to reach a target maturity at a scheduled intake date of the food based on the maturity of the food. According to the determination, the at least one processor may control at least one of temperature, humidity, and gas composition ratio in the storage space by using a controller configured to control at least one of temperature, humidity, and gas composition ratio.

The at least one processor calculates the time when the maturity of the food is determined and the estimated time required until the scheduled intake date of the food, determines acceleration of maturation if the temperature at the time when the maturity of the food is determined is not high enough to reach a target maturity at the scheduled intake date, and determines the deceleration of maturation if the temperature is high enough to exceed the target maturity at the scheduled intake date.

In addition, when it is determined that acceleration or deceleration of maturation of the food is necessary, the at least one processor may increase or decrease a temperature in the storage space from a preset temperature during at least a portion of a period between the time when the maturity of the food is determined and the scheduled intake date.

The maturation rate is related to the temperature, humidity, and gas composition ratio of the surrounding environment. For example, when the temperature is increased, the humidity is decreased, or the oxygen ratio in the gas is increased, the maturation rate increases, and when the temperature is decreased, the humidity is increased, or the oxygen ratio in the gas is decreased, the maturation rate decreases.

For example, when acceleration of maturation of food is required, the at least one processor may accelerate a chemical reaction for maturation by increasing the temperature in the storage space. Thus, the maturation of food may be accelerated. When a deceleration of maturation of food is necessary, the at least one processor may slow the chemical reaction for maturation by reducing the temperature in the storage space. Thus, the maturation of food may be decelerated.

When acceleration or deceleration of maturation of food is required, the at least one processor may calculate a temperature difference between the temperature in the storage space at the time when the maturity of the food is determined and the temperature at which the target maturity may be reached on the scheduled intake date, and may increase or decrease the temperature in the storage space by the corresponding temperature difference. In this case, the user may acquire the food of a desired maturity on the intake date, and thus, such a case that additional maturation time is required due to insufficient maturation or the taste or texture of food is deteriorated due to excessive maturation may not occur.

In addition, when the temperature in a storage space is increased or decreased from a preset temperature in order to accelerate or decelerate the maturation of food, the at least one processor may change the temperature in the storage space to a preset temperature or a temperature set by the user for intake or cooking before the user intakes or cooks. In this case, because the user may acquire food at a suitable temperature for intake or cooking, the time required for heating or cooling food, such as defrosting frozen food for intake or cooking is reduced.

The processing of food by the at least one processor described above may be performed by a separate processor provided in the refrigerator in addition to the at least one processor included in the food monitoring apparatus.

Figure 8:
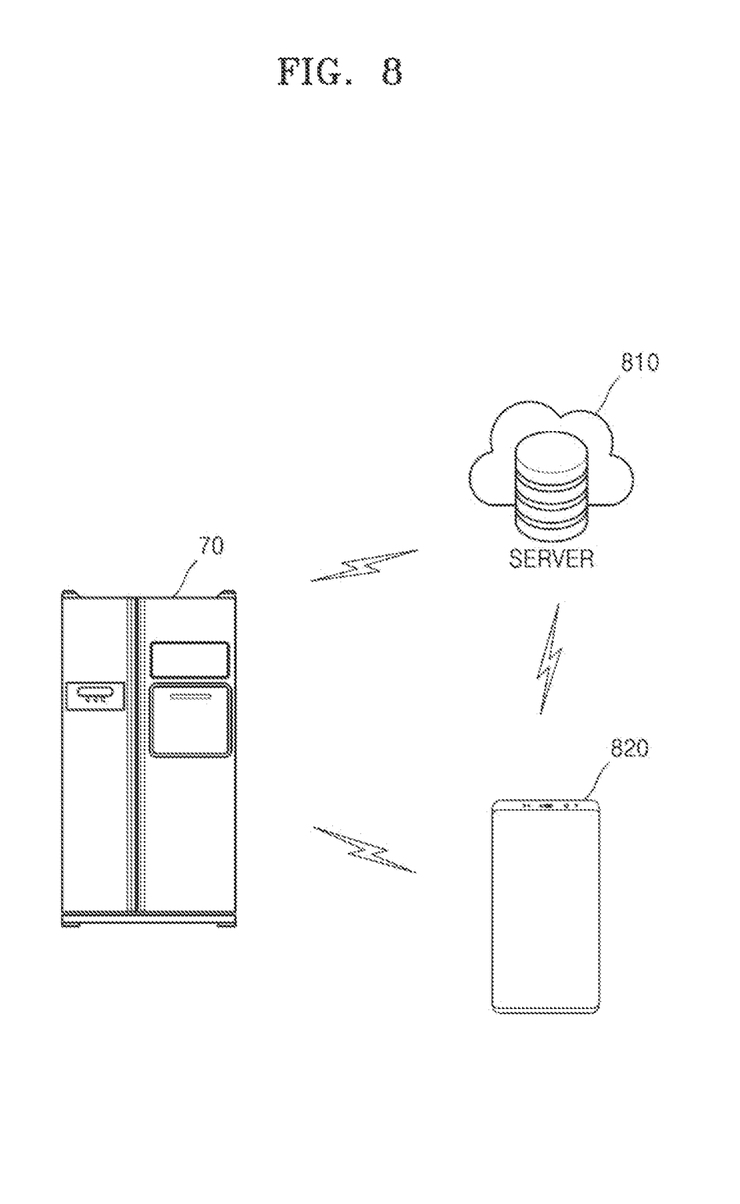
FIG. 8 is a conceptual diagram of a refrigerator further including a communication interface for communicating with an external apparatus according to example embodiments.

FIG. 8 is a conceptual diagram of a refrigerator further including a communication interface for communicating with an external apparatus according to example embodiments.

Referring to FIG. 8, the refrigerator 70 may include a communication interface that communicates with an external apparatus to transmit second information to the external apparatus. The refrigerator 70 may communicate with a server 810 and/or a mobile terminal 820 through the communication interface. The communication interface may include a short-range wireless communication interface, a mobile communication unit, and the like. The short-range wireless communication interface includes a Bluetooth communication unit, a Bluetooth Low Energy (BLE) communication unit, a Near Field Communication interface, a WLAN (Wi-Fi) communication unit, a Zigbee communication unit, an infrared Data Association (IrDA) communication unit, a Wi-Fi Direct (WFD) communication unit, an ultra wideband (UWB) communication unit, an Ant+ communication unit, etc., but is not limited thereto.

The refrigerator 70 including a communication interface configured to communicate with an external apparatus allows a user to monitor information about the state of food in the storage space without restrictions on location and time by transmitting information about the state of food to the mobile terminal 820 of the user. In addition, information about food from a plurality of refrigerators 70 may be provided to the server 810, and it may be easier for a user to determine and manage the state of a large amount of arbitrary products. Thus, the refrigerator 70 including a communication interface communicating with external apparatuses may also be applied to distribution management.

Figure 9:
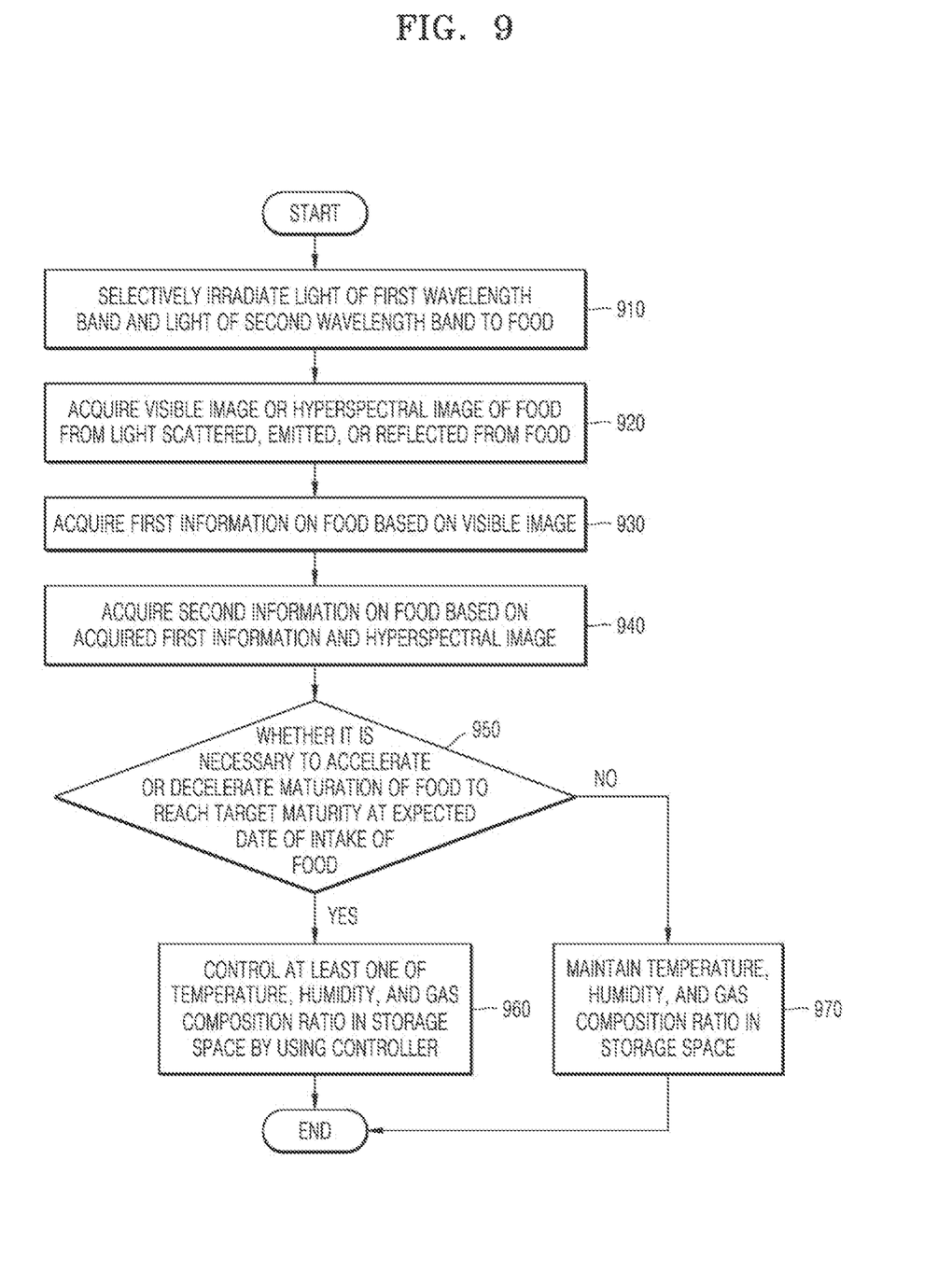
FIG. 9 is a flowchart illustrating a method of controlling at least one of temperature, humidity, and gas composition ratio in a storage space by a refrigerator according to example embodiments.

FIG. 9 is a flowchart illustrating a method of controlling at least one of temperature, humidity, and gas composition ratio in a storage space by a refrigerator according to example embodiments.

Referring to FIG. 9, the method of controlling at least one of temperature, humidity, and gas composition ratio in the storage space by the refrigerator includes operations performed in a time series in the refrigerator 70 illustrated in FIGS. 7 and 8. Accordingly, the descriptions given with respect to FIGS. 7 and 8, even though omitted below, may be applied to the method of controlling at least one of temperature, humidity, and gas composition ratio in the storage space of the refrigerator of FIG. 9.

In addition, the method of FIG. 9 may be performed by a food monitoring apparatus (e.g., the food monitoring apparatus 10 of FIG. 1 or 2) included in a refrigerator (e.g., the refrigerator 70 of FIG. 7 or 8), or may be performed by a separate processor outside the food monitoring apparatus. When the method of FIG. 9 is performed by the food monitoring apparatus, the method of FIG. 9 may be performed by arbitrary components included in the food monitoring apparatus (e.g., the at least one processor 130 of FIG. 1 or 2).

In operation 910, the refrigerator may selectively radiate light of a first wavelength band to food and light of a second wavelength band that is different from the first wavelength band by using at least one light source. Operation 910 of FIG. 9 corresponds to operation 610 of FIG. 6, and thus, repeated descriptions thereof are omitted.

In operation 920, the refrigerator may acquire a visible image or a hyperspectral image of the food from light scattered, emitted, or reflected from the food by using at least one image sensor. Operation 920 of FIG. 9 corresponds to operation 620 of FIG. 6, and thus, repeated descriptions thereof are omitted.

In operation 930, the refrigerator may acquire first information on the food based on the visible image. Operation 930 of FIG. 9 corresponds to operation 630 of FIG. 6, and thus, repeated descriptions thereof are omitted.

In operation 940, the refrigerator may acquire second information on the food based on the acquired first information and the hyperspectral image. Operation 940 of FIG. 9 corresponds to operation 640 of FIG. 6, and thus, repeated descriptions thereof are omitted.

In operation 950, if the second information includes the maturity of food, the refrigerator determines whether acceleration or deceleration of maturation of the food is necessary to reach a target maturity at the scheduled intake date of the food based on the maturity of the food. For example, the refrigerator calculates the time when the maturity of the food is determined and the estimated time required until the scheduled intake date of the food, determines acceleration of maturation if the temperature at the time when the maturity of the food is determined is not high enough to reach a target maturity at the scheduled intake date, and determines the deceleration of maturation if the temperature is high enough to exceed the target maturity at the scheduled intake date.

In operation 960, when it is determined that acceleration or deceleration of maturation of food is necessary, the refrigerator may control at least one of temperature, humidity, and gas composition ratio in a storage space by using a controller configured to control at least one of temperature, humidity, and gas composition ratio. For example, the refrigerator may increase or decrease the temperature in a storage space from a preset temperature during at least a portion of a period between the time when the maturity of the food is determined and the scheduled intake date.

The refrigerator may calculate a temperature difference between a temperature in a storage space at a time when the maturity of food is determined and a temperature that may reach a target maturity on a scheduled intake date, and may increase or decrease the temperature in the storage space by the corresponding temperature difference. In addition, when the temperature in a storage space is increased or decreased from a preset temperature in order to accelerate or decelerate the maturation of food, the refrigerator may change the temperature in the storage space to a preset temperature or a temperature preferred by the user for intake or cooking before the user intakes or cooks.

In operation 970, when it is determined that acceleration or deceleration of maturation of the food is not required, the refrigerator may maintain the temperature, humidity, and gas composition ratio in the storage space.

Although example embodiments have been described in detail above, the scope is not limited thereto, and various modifications and improvements by those skilled in the art using the basic concept defined in the following claims. It should be understood that example embodiments described herein should be considered in a descriptive sense only and not for purposes of limitation. Descriptions of features or aspects within each example embodiment should typically be considered as available for other similar features or aspects in other embodiments.

While examples embodiments have been described with reference to the figures, it will be understood by those of ordinary skill in the art that various changes in form and details may be made therein without departing from the spirit and scope as defined by the following claims and their equivalents.

What is claimed is:

1. A food monitoring apparatus comprising:
at least one light source configured to selectively radiate light of a first wavelength band and light of a second wavelength band that is different from the first wavelength band to food;
at least one image sensor configured to obtain a visible image of the food and a hyperspectral image of the food based on light scattered, emitted, or reflected from the food; and
at least one processor configured to obtain first information of the food based on the visible image, and to obtain second information of the food based on the first information and the hyperspectral image,
wherein the at least one processor is further configured to obtain at least one parameter representing a content of an indicator material included in the food from the hyperspectral image, the indicator material emitting fluorescence based on the light radiated by the at least one light source, and
wherein the at least one processor is further configured to correct, based on the first information of the food obtained based on the visible image, a value of the at least one parameter obtained from the hyperspectral image, and obtain the second information based on the corrected value of the at least one parameter.

2. The food monitoring apparatus of claim 1, wherein the at least one processor is further configured to further correct, based on the first information, at least one of the hyperspectral image, and a correlation between the at least one parameter and the second information.

3. The food monitoring apparatus of claim 2, wherein the first information includes at least one of a type of the food and a part of the food, and
wherein the at least one processor is further configured to selectively apply a weight to the at least one parameter based on the first information, and obtain the second information by analyzing the hyperspectral image based on the at least one parameter to which the weight is applied.

4. The food monitoring apparatus of claim 2, wherein the first information includes a packaging condition of the food, and
wherein the at least one processor is further configured to correct the at least one parameter based on the packaging condition, and obtain the second information based on the corrected at least one parameter.

5. The food monitoring apparatus of claim 2, wherein the at least one parameter includes at least one of 1,4-dihydronicotinamide adenine dinucleotide (NADH) content, porphyrin content, flavin adenine dinucleotide (FAD) content, and collagen content included in the food.

6. The food monitoring apparatus of claim 1, wherein the first information includes a location of the food in the food monitoring apparatus, and
wherein the at least one processor is further configured to:
control the at least one light source to radiate the light of the second wavelength band to an area of the food monitoring apparatus corresponding to the location of the food; and
obtain the hyperspectral image from light received from the area of the food monitoring apparatus corresponding to the location of the food.

7. The food monitoring apparatus of claim 1, wherein the first wavelength band ranges from 400 nm to 700 nm,
wherein the second wavelength band ranges from 250 nm to 400 nm, and
wherein the at least one image sensor is further configured to measure light in a wavelength band ranging from 300 nm to 700 nm.

8. A refrigerator comprising:
a main body comprising a storage space;
a door configured to open and close the storage space; and
the food monitoring apparatus according to claim 1 that is disposed in the storage space.

9. The refrigerator of claim 8, wherein the second information includes at least one of freshness, maturity, and spoilage of the food, and
wherein the at least one processor is further configured to determine at least one of whether the food is edible, an intakeable period of the food, an optimum intake time of the food, and a cooking method of the food based on the at least one of the freshness, maturity, and spoilage of the food.

10. The refrigerator of claim 8, further comprising a controller comprising at least one processor and configured to control at least one of temperature, humidity, and gas composition ratio in the storage space.

11. The refrigerator of claim 10, wherein the second information includes maturity of the food, and
wherein the at least one processor is further configured to:
determine whether acceleration or deceleration of maturation of the food is necessary to reach a target maturation at a preset intake time of the food based on the maturity of the food; and
control the at least one of temperature, humidity, and gas composition ratio in the storage space by the controller.

12. The refrigerator of claim 11, wherein, when it is determined that acceleration or deceleration of maturation of the food is necessary, the at least one processor is further configured to increase or decrease a temperature in the storage space from a preset temperature during at least a portion of a period between a time when the maturity of the food is determined and the preset intake time.

13. The refrigerator of claim 8, further comprising a display device disposed on the door, the display device configured to output the second information received from the food monitoring apparatus.

14. The refrigerator of claim 8, further comprising a communication interface configured to communicate with an external device to transmit the second information to the external device.

15. A method of operating a food monitoring apparatus, the method comprising:
selectively radiating light of a first wavelength band and light of a second wavelength band that is different from the first wavelength band to food by at least one light source;
obtaining a visible image of the food and a hyperspectral image of the food based on light scattered, emitted, or reflected from the food by at least one image sensor;
obtaining first information of the food based on the visible image; and
obtaining second information of the food based on the first information and the hyperspectral image,
wherein the obtaining the second information includes:
obtaining at least one parameter representing a content of an indicator material included in the food from the hyperspectral image, the indicator material emitting fluorescence based on the light radiated by the at least one light source;
correcting, based on the first information of the food obtained based on the visible image, a value of the at least one parameter obtained from the hyperspectral image; and
obtaining the second information based on the corrected value of the at least one parameter.

16. The method of claim 15, wherein the obtaining of the second information includes correcting, based on the first information, at least one of the hyperspectral image, and a correlation between the at least one parameter and the second information.

17. The method of claim 16, wherein the first information includes at least one of a type of the food and a part of the food, and
wherein the obtaining of the second information includes selectively applying a weight to the at least one parameter based on the first information, and obtaining the second information by analyzing the hyperspectral image based on the at least one parameter to which the weight is applied.

18. The method of claim 16, wherein the first information includes a packaging condition of the food, and
wherein the obtaining of the second information includes correcting the at least one parameter based on the packaging condition, and obtaining the second information based on the corrected at least one parameter.

19. The method of claim 16, wherein the at least one parameter includes at least one of 1,4-dihydronicotinamide adenine dinucleotide (NADH) content, porphyrin content, flavin adenine dinucleotide (FAD) content, and collagen content in the food.

20. The method of claim 15, wherein the first information includes a location of the food in the food monitoring apparatus, and
wherein the obtaining of the visible image of the food or the hyperspectral image of the food includes controlling the at least one light source to radiate light of the second wavelength band to an area of the food monitoring apparatus corresponding to the location of the food, and obtaining the hyperspectral image based on light received from the area of the food monitoring apparatus corresponding to the location of the food.

* * * * *